United States Patent [19]

Fontanella et al.

[11] Patent Number: 4,528,297
[45] Date of Patent: Jul. 9, 1985

[54] NEUROLEPTIC 3-AZETIDINYLETHYL-1-PHENYL-2-IMIDAZOLIDINONES

[75] Inventors: Luigi Fontanella, Sassari, Italy; Edoardo Martinelli, Zurich, Switzerland; Alessandro Assandri, Mariano Comense, Italy

[73] Assignee: Gruppo Lepetit S.p.A., Italy

[21] Appl. No.: 471,988

[22] Filed: Mar. 4, 1983

[30] Foreign Application Priority Data

Mar. 9, 1982 [IT] Italy ............................ 20019 A/82

[51] Int. Cl.$^3$ .................. A61K 31/415; C07D 403/06
[52] U.S. Cl. .................................... 514/392; 548/318
[58] Field of Search .................... 548/318; 424/273 R

[56] References Cited

U.S. PATENT DOCUMENTS 4,011,238  3/1977  Fontanella et al. ............... 548/318

FOREIGN PATENT DOCUMENTS 624312   3/1963  South Africa .................... 548/318
1383619  2/1975  United Kingdom ............... 548/318

*Primary Examiner*—Richard A. Schwartz
*Attorney, Agent, or Firm*—William J. Stein; Stephen L. Nesbitt; Francesco Macchetta

[57] ABSTRACT

New 3-azetidinylethyl-1-phenyl-2-imidazolidinones with neuroleptic activity, their use and methods for their preparation. The azetidinyl group bears alkyl substituents in position 3 and the phenyl group bears halogenated substituents in position 3 and hydroxy group or acylated hydroxy groups in position 4 and/or 6.

4 Claims, No Drawings

NEUROLEPTIC 3-AZETIDINYLETHYL-1-PHENYL-2-IMIDAZOLIDINONES

The present invention is directed to new neurolepetic-3-azetidinylethyl-1-phenyl-2-imidazolidinone derivatives of formula

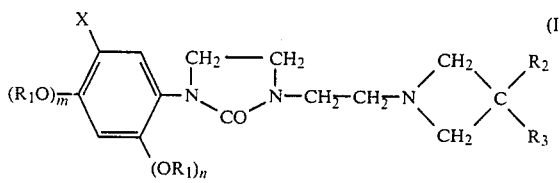

wherein X represents chloro, bromo or fluoro, m and n, independently, represent zero or 1 with the proviso that they cannot represent simultaneously zero, $R^1$ represents hydrogen or a $(C_1-C_{20})$acyl group which may contain from 1 to 3 unsaturated carbon-carbon bonds, $R_2$ and $R_3$ independently represents a $(C_1-C_4)$alkyl group, and the pharmacologically acceptable acid addition salts thereof.

South African Pat. No. 62/4312 describes neuroleptic imidazolidinones which do not contain the azetidinylethyl group.

British Pat. No. 1,383,619 describes neurolpetic 3-azetidinylethyl-1-phenyl-2-imidazolidinones wherein the phenyl group is optionally substituted with one or more substituents selected from $(C_1-C_4)$alkyl, halogen, alkoxy, and trifluoromethyl.

The novel compounds of the invention possess a considerable long-lasting neuroleptic activity. Moreover, they are substantially devoid of the undesired side-effects that are generally found in neuroleptic substances, including those mentioned above. These novel compounds also possess a very low toxicity and, therefore, show a high therapeutic index. The preferred compounds of the invention are those of formula I wherein X represents chloro, m represents 1 and n represents zero, $R^1$ is hydrogen or an acyl group selected from acetyl, butyryl, pivaloyl, enanthyl, decanoyl, undecyl, palmityl, and stearyl; $R^2$ and $R^3$ are methyl, ethyl, propyl or butyl groups. As herein used, the terms "pharmacologically acceptable acid addition salts" refer to acid addition salts of the compounds of the formula I with non-toxic pharmaceutically acceptable acids, wherein the anions are essentially safe for animals, when administered at a dose at which the corresponding salt is active as a neuroleptic agent. In so doing, the positive effects of the free base are not impaired by undesirable side-effects due to the anions. Pharmaceutically acceptable addition acids include mineral acids such as hydrochloric or sulfuric acid, and organic acids such as lactic, succinic, fumaric, glutaric, citric, malic, pamoic, p-toluenesulfonic, methansulfonic, tartaric and similar acids.

It is known that the neuroleptic drugs, the so called "major tranquillizers", possess biochemical effects which are related to neuroendocrinologic alterations, such as a considerable increase of the serum prolactin. The increase is characterized by an increase in the plasma level of dopamine (DA) metabolites such as homovanillic acid (HVA) and dihydroxy-phenylacetic (DOPAC) acids. This activity, which is a signal of a DA increased turnover due to the blockage of dopaminergic receptors, was demonstrated in the brain and in particular in some cerebral areas as of experimental animals and, after treatment with neuroleptics, in the cerebrospinal fluid of psycotic patients. An abnormal increase of plasma prolactin may be correlated with amenorrhea, galactorrhea, libido decrease, or decrease of the spermatoza concentration in the seminal fluid. (See: M. T. Buckman et al., in JAMA, Vol. 236 No. 7, page 871, (1976); and P. Falaschi et al., Clin. Endocrinol. 8, No. 5, 427, (1978)).

Is is therefore evident that a need for neuroleptic substances exists, which in addition to their specific long-lasting anti-psychotic action, do not possess, or possess to a minimum extent, the above characteristic side-effects. Representative experiments made with the compounds of the invention demonstrate that they are highly active in tests which are predictive of neuroleptic activity in humans, such as the inhibition of the conditioned response in rats, the inhibition of the specific effects of amphetamine in rats, the inhibition of apomorphine emesis in dogs. (See, for instance, D. E. Clody, B. Beer, "Predictability in Psycopharmacology: Preclinical and Clinical Correlations", Raven Press New York, 1975, page 214; J. M. van Rossum, et al.; "The Neuroleptics, Modern Problems of Pharmacopsychiatry, Modern Problems of Pharmacopsychiatry", S. Karger, Basel, 1970, pages 28–29).

In the "apomorphine emesis inhibition test" in dogs, the compound of example 1 determines a 70% emesis inhibition 30 minutes after the oral administration of 0.1 mg/Kg to 5 animals. In other words, the mean number of emesis in five animals is reduced by 70% when the above dosage is given before a subcutaneous administration of 0.1 mg/Kg apomorphine sulphate. The experiment is conducted substantially as described by G. Chen. et al., J. Pharmacol. Exptl. Ther. 98, 245, (1950). The compound of example 1 when given (i.p.) 100 mg/Kg in mice does not provoke the death of the treated animals. The compound 1-(3-chlorophenyl)-3-[2-(3,3-dimethylazetidin-1-yl)ethyl]-2-imidazolidinone, which is described in British Pat. No. 1,383,619, shows a 70% inhibition of the apomorphine emesis under the same experimental conditions as above, but it provokes 100% deaths of the treated animals when given i.p. 100 mg/Kg in mice.

Surprisingly, the compound of example 1 is still active (65% emesis inhibition) 6 hours after its administration under the experimental conditions described above. A study was carried out to evaluate the turnover rate of dopamine (DA), the increase of dihydroxyphenylacetic acid (DOPAC) levels in male Wistar rat striatum after 1 mg/Kg i.p. administration of the neuroleptic substance. The animals weighed 200–230 g. The DOPAC level was measured according to J. W. Kebabian et al., Journal of Neurochemistry 28, 795, (1977). In a comparative test the compound of example 1 does not provoke any increase of DOPAC level in the five treated animals, while compound 1-(3-chlorophenyl)-3-[2-(3,3-dimethylazetidin-1-yl)ethyl]-2-imidazolidinone provokes a 50% average increase (treated versus controls) of DOPAC level. In another group of representative tests, prolactin levels were radioimmunologically determined using the materials and the methods of the National Institute of Arthritis, Metabolism, and Digestive Diseases, (N.I.A.M.D.D.) [National Institute of Health (N.I.H.), Bethesda, Md., USA], as a part of a study for evaluating the distribution of the pituitary hormones in rats. Plasma prolactin levels were calculated 60 minutes after the i.p. administration of the test substance. In the above test, the compound of example 1 does not provoke any prolactin level increase, while, the 1-(3-chlorophenyl)-3-(2-(3,3-dimethylazetidin-1-yl)ethyl)-2-imidazolidinone does provoke a 100% increase of the prolactin level in the treated animals over the controls which are given only the vehicle.

The compounds of the invention are conveniently prepared according to the procedures described in British Pat. No. 1,383,619 for the preparation of the intermediate compound of formula II

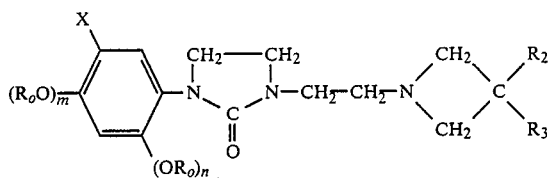

wherein $R_o$ represents an easily removable protecting group of the hydroxy function of a phenol group, m and n are independently zero or 1, provided that m and n are not zero, simultaneously X represents chloro, bromo or fluoro, and $R^2$ and $R^3$ independently represent a $(C_1-C_4)$alkyl group.

$R_o$ is preferably selected from lower alkyl, benzyl and substituted benzyl group. As a representative example, the 1-(3-chloro-4-methylphenyl)-3-[2-(3,3-dimethylazetidin-1-yl)ethyl]imidazolidinone is conveniently prepared from 1-(3-chloro-4-methoxyphenyl)-2-imidazolidinone by reacting it with 1-(2-haloethyl)-3,3-dimethylazetidine as outlined in the scheme below, wherein X is chloro, $R_o$, $R_2$ and $R_3$ are methyl, and "halo" represents chloro or bromo atoms.

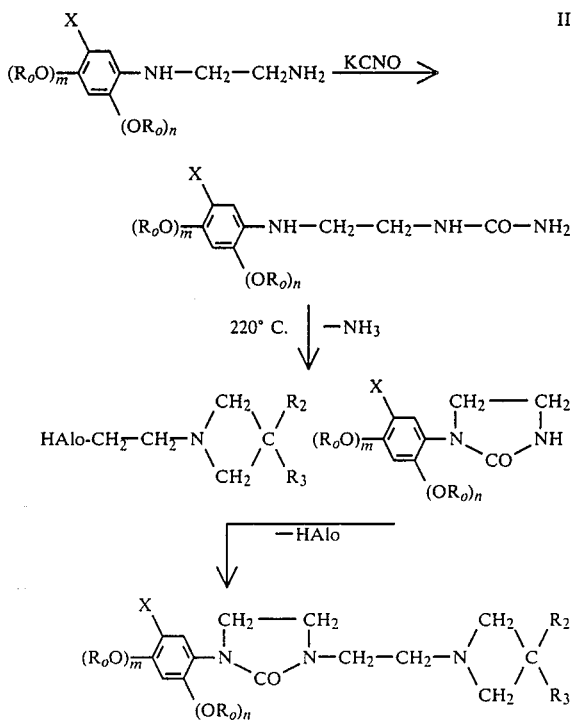

The intermediates of formula II for all the compounds of the invention can be prepared according to the process outlined in the above scheme, wherein $R_o$, X, $R_2$, and $R_3$ are as defined for the compounds of the present invention.

For preparing the compounds of formula I, the compounds of formula II are treated according to a variety of known-per-se techniques. The compounds of formula II are in fact easily transformed into the compounds of formula I by hydrolysis of the phenol-ether bond. A variety of such methods are known for the dealkylation of arylalkyl ethers and can be used for hydrolyzing the compounds of formula II wherein $R_o$ is methyl or lower alkyl. In particular, the method described by G. I. Feutrill et al. in Tetrahedron Letters No. 16, 1327, (1970) and which concerns the use of thioethoxy ions in dimethylformamide under heating, is particularly advantageous since it does not provoke any chemical interference with the other functions of the molecule.

Another convenient process is that based on the use of sodium p-thiogenate, which was described by (C. Hansson et al., in Synthesis 1976, page 191).

The compounds of formula I wherein $R^1$ is hydrogen are in turn transformed into the corresponding derivatives wherein $R^1$ is an acyl group as defined above by reacting the selected compound with a suitable acyl derivative according to the methods known in the art. Such acyl derivatives include acyl halides, anhydrides, mixed anhydrides, esters which easily exchange their alcohol group with the phenols, and the like.

The procedures for preparing the intermediate substituted-1-phenyl-2-imidazolidinones and 1-(2-haloethyl)azetidines are described in detail respectively by W. B. Wright et al., in J. Med. Chem. 9, 852, (1966) and E. Testa et al., in Liebigs Ann. Chem. 635, 119 (1960) and 633, 56 (1960). Other objects of the present invention are methods of use and pharmaceutical compositions for the therapeutic treatment of neurosis by administering a psychoactive amount of at least one compound of the invention to a patient in need.

As used herein "psychoactive amount" means an amount which is able to produce a neuroleptic activity when administered to a patient who suffers from psychosis or neurosis.

The "psychoactive amount" depends on various parameters, such as the kind of patients, their weight, age, sex, and diet, the specific compound or compounds to be used, the route of administration, the frequency of the treatment, the severity of the neurosis or psychosis, and the fact that the medicine is administered to patients who have eaten or to fasted patients. According to the methods of the invention a psychoactive amount of one or more compounds of the invention is administered to a patient with mental disorders so that an antipsychotic effective amount of the medicine distributes into the blood, crosses the hematoencephalic barrier and reaches the target brain tissues. The administration may be parenteral (intravenous, intraperitoneal, subcutaneal, intramuscular, etc.), oral or rectal. The active compounds are administered daily at doses ranging between about 0.2 to about 3 mg/Kg. A preferred dosage range is 0.5–2 mg/Kg. Higher doses can be used for instance when orally administering a compound of the invention in a long-acting oral form.

In psychotic patients the psychoactive dosage is preferably administered at predetermined intervals of time. The individual dosage should be the minimum psychoactive dose which gives an adequate psychoactive blood level of the drug.

According to the invention, at least one compound of the invention is incorporated as the active ingredient in a pharmaceutical composition which comprises from 0.001 to about 95% by weight of the active compound in an admixture with a pharmaceutically-acceptable vehicle. The term "pharmaceutically-acceptable vehicle" refers to pharmaceutical ingredients known to be useful for preparing pharmaceutical compositions to be administered to patients in need. Such ingredients are safe and non-sensitizing under the conditions used.

Suitable pharmaceutically-acceptable vehicles are known and reported in reference books such as "the Remington's Pharmaceutical Sciences", 15th Ed. Mack Publishing Co., Easton, Pa., USA, (1975). They include acacia gum, starch, dextrose, lactose, talcum, stearic acid, magnesium stearate, polyethyleneglycols and tragacanth gum. The pharmaceutical compositions can be formulated into tablets, capsules, pills, sugar-coated tablets, elixirs, syrups, emulsions, dispersions, wettable- or effervescent powders, aseptic injectable compositions, and may contain suitable known adjuvants. The oral formulations are preferred and the active compound may be formulated also in sustained-release, or entero-coated tablets or capsules. Among the preferred formulations there are the sterile injectable compositions which contains from 0.0001 to about 10% by weight of the active compound in a suitable pharmaceutically-acceptable carrier such as isotonic saline, injectable Ringer USP, injectable sodium lactate Ringer USP, and the like.

The following examples better illustrate the invention and some ways of utilizing it, however they should not be cconstrued as imposing any limitation on the scope of the invention.

EXAMPLE 1

1-(3-Chloro-4-hydroxyphenyl)-3-[2-(3,3-dimethylazetidin-1-yl)ethyl]-2-imidazolidinone and the hydrochloride thereof Ethanthiole (32 ml) in anhydrous dimethylformamide (200 ml) is carefully added to 55% sodium hydride in mineral oil (10 g) in anhydrous dimethylformamide (600 ml), under a nitrogen stream. When the bubbling of hydrogen produced by the reation mixture is over, 1-(3-chloro-4-methoxyphenyl)-3-[2-(3,3-dimethyl-azetidin-1-yl)ethyl]-2-imidazolidinone (20 g) is added to the reaction mixture. Then, it is stirred for about 2 hours at 100° C., cooled and concentrated under reduced pressure. The residue is picked up with ethanol, dissolved in water and acidified by adding concentrated hydrochloric acid. The aqueous phase is then extracted with ethyl ether while the insolubles are separated by filtration. Ammonium hydroxide is then added to adjust the pH to an alkaline value, and a precipitate begins to form. The solid residue is collected by filtration, washed with ethyl ether and dried under reduced pressure at about 80° C. to yield 16.2 g (84%) of the product of the title. M.p. 174°–177° C.

IR, NMR, and elemental analysis data confirm the chemical structure of this product.

A sample (13 g) of the product is then dissolved in chloroform and hydrogen chloride in ethyl ether is added thereto. Upon cooling, the hydrochloride of the product of the title (13.7 g) crystallizes and is collected by filtration. M.p. 212°–214° C.

EXAMPLE 2

1-(4-Acetoxy-3-chlorophenyl)-3-[2-(3,3-dimethylazetidin-1-yl]ethyl-2-imidazolidinone Acetic anhydride (0.11 g) is added to 1-(3-chloro-4-hydroxyphenyl)-3-[2-(3,3-dimethylazetidin-1-yl]ethyl)-2-imidazolidinone (0.32 g) in 0.1N sodium hydroxide (15 ml) under stirring while keeping the mixture at 0° C. Stirring is continued and after 30 minutes the precipitate which forms is collected by filtration and washed with cold water. It crystallizes from ethyl ether (yield=0.20 g). M.P. 118°–119° C. NMR, IR, mass spectra confirm the chemical structure of the product.

EXAMPLE 3

1-(3-Chloro-4-methoxyphenyl)-3-[2-(3,3-dimethylazetidin-1-yl)ethyl]-2-imidazolidinone 1-(3-Chloro-4-methoxyphenyl)-2-imidazolidinone (26.5 g) in dimethylformamide (230 ml) is added to a suspension of 55% sodium hydride in mineral oil (6.6 g) in anhydrous dimethylformamide (DMF) (85 ml) at about 25° C., with stirring.

After about 90 minutes, 1-(2-chloroethyl)-3,3-dimethylazetidine (20.7 g) in DMF (70 ml) is added thereto and the mixture is heated to about 80° C. 2 Hours later, the mixture is cooled, the insolubles are separated by filtration, and the filtrate is concentrated under reduced pressure. Upon cooling, a precipitate forms which is washed and dried, yielding 39 g (100%) of the product of the title, M.p. 93°–95° C.

EXAMPLE 4

1-(3-Chloro-4-methoxyphenyl)-2-imidazolidinone (a) 2-Bromoethylamine hydrobromide (105 g) in ethanol (260 ml) is added to a solution of 3-chloro-4-methoxyaniline (80 g) in ethanol (1.5 l) and N,N-dimethylaniline (132 ml).

The reaction mixture is heated for 24 hours and then cooled. A precipitate (66.4 g) forms which is collected by filtration. Another crop of this product, which upon analysis was shown to be N-(3-chloro-4-methoxyphenyl)-1,2-ethylendiamine hydrobromide, is obtained by concentration of the mother liquors. The overall yield is 92.2 g (64%). Crystallization from ethanol, M.p. 207° C., (b) 56 g of the above intermediate is dissolved in warm water and then, after cooling to 28°–30° C., 17 g of potassium cyanate is added thereto. The mixture is refluxed for about 2.5 hours then it is cooled and N-[2-[(3-chloro-4-methoxyphenyl)amino]-ethyl]urea is collected by filtration.

Yield=39 g. M.p. 140°–142° C. (acetone).

(c) N-[2-[-3-(chloro-4-methoxyphenyl)amino]ethyl]urea (5 g) is heated to 210°–230° C. for about 1 hour. After cooling, the reaction is dissolved in acetone and the temperature is then lowered to 0° C.

The product of the title is subsequently recovered by filtration (3.8 g; 81,7%). The obtained 1-(3-chloro-4-methoxyphenyl)-2-imidazolidinone melts at 187°–189° C.

EXAMPLE 5

1-(3-chloro-4-decanoyloxyphenyl)-3-[2-(3,3-dimethylazetidin-1-yl)ethyl]-2-imidazolidinone 1-(3-Chloro-4-hydroxyphenyl)-3-[2-(3,3-dimethylazetidin-1-yl)ethyl]-2-imidazolidone hydrochloride (1.8 g) is dissolved in ethanol (30 ml) and added to a solution of potassium hydroxide (0.6 g) in ethanol (30 ml). The mixture is heated until the solid is dissolved, and then concentrated under reduced pressure. The residue is washed with benzene and taken up with tetrahydrofuran (THF). Decanoyl chloride (1 g) in THF (20 ml) is added to the mixture and stirred. Then the mixture is concentrated, the residue is collected, washed with water, and concentrated ammonium hydroxide is added thereto. After extraction with ethyl ether the pooled organic layer is washed with 10% sodium hydroxide and then evaporated to dryness. The residue is dissolved in methylene chloride and purified by column chromatography using a silica gel column (25 g) and eluting with 2% methanol methylene chloride. The first eluted fractions are discarded and then, upon elution with 4% methanol methylene chloride, the fractions which contains the product of the title are collected and the product is recovered as common in the art. Yield=0.21 g.

M.p. 60.5° C.

Elemental analysis, IR and NMR spectra confirm the chemical structure of the product.

EXAMPLE 6

1-(3-Chloro-4-hydroxyphenyl)-3-[2-(3,3-dibutylazetidin-1-yl)ethyl]-2-imidazolidinone Ethanol(12.8 ml) in anhydrous DMF (80 ml) is added to a suspension of 55% sodium hydroxide in mineral oil (4 g) in 200 ml of DMF, under stirring and a continuous nitrogen stream at 10° C. When the development of hydrogen is completed, 10 g of 1-(3-chloro-4-methoxyphenyl)-3-[2(3,3-dibutylazetidin-1-yl)ethyl]-2-imidazolidinone are added.

The mixture is heated to 100° C. for 3 hours, and the reaction is monitored by thin layer chromatography (methanol:chloroform, 2:8).

The solvent is then removed by distillation under reduced pressure and the solid residue is taken up with ammonium hydroxide and extracted with methylene chloride. The organic layer is then washed with water and evaporated to dryness. The white product of the title is thus obtained. (9.2 g; 81%).

M.p. 172°-173° C.

The elemental analysis, IR NMR, and mass spectra are in accordance with the proposed chemical structure.

EXAMPLE 7

1-(3-Chloro-4-methoxyphenyl)-3-[2-(3,3-dibutylazetidin-1-yl)ethyl]-2-imidazolidinone 1-(3-Chloro-4-methoxyphenyl)-2-imidazolidinone (11.7 g) is reacted with 1-(2-chloroethyl)-3,3-dibutylazetidine substantially as described in Example 3.

Yield 20 g M.p. 77°-78° C.

1-(2-Chloroethyl)-3,3-dibutylazetidine (p.e. 85° C./0.05 mmHg) is obtained by reacting 1-(2-hydroxyethyl)-3,3-dibutylazetidine with thionyl chloride.

EXAMPLE 8

1-(3-Chloro-6-hydroxyphenyl)-3-[2-(3,3-dimethylazetidin-1-yl)ethyl]-2-imidazolidinone Essentially following the procedure of Example 1, but using 1-(3-chloro-6-methoxyphenyl)-3-[2-(3,3-dimethylazetidin-1-yl)ethyl]-2-imidazolidinone instead of 1-(3-chloro-4-methoxyphenyl)-3-[2-(3,3-dimethylazetidin-4-yl)ethyl]-2-imidazolidinone, the product of the title is obtained. Upon NMR analysis it shows the following wing main peaks ($^1$H NMR; 270 MHz in DMSO-$d_6$, $\delta$): 1,20; 2,75; 3,20; 3,36; 3,52; 3,78; 6,91, (H-5'); 7,13 (H-4'); e 7,25 (H-2') M.p. 117° C. (ethyl ether).

M.p. of the corresponding hydrochloride: 173°-174° C.

I.R., NMR, and mass spectra are in agreement with the proposed structure.

The starting 1-(3-chloro-6-methoxyphenyl)-3-[2-(3,3-dimethylazetidin-1-yl)ethyl]-2-imidazolidinone is prepared according to the procedure described in Example 3 starting from 1-(3,3-chloro-6-methoxyphenyl)-2-imidazolidinone, which is in turn prepared from 3-chloro-6-methoxyaniline as described in Example 4.

EXAMPLE 9

1-(3-Chloro-6-hydroxy-4-methoxyphenyl)-3-[2-(3,3-dimethylazetidin-1-yl)ethyl]-2-imidazolidinone Starting from 3-chloro-4,6-dimethoxyaniline and essentially following the procedures of Examples 4, 3 and 1, but using a deficit of ethanthiole, M.p. 138° C. (ethyl acetate).

NMR and mass spectra are in agreement with the proposed structure.

EXAMPLE 10

1-(3-Chloro-4,6-dihydroxyphenyl)-3-[2-(3,3-dimethylazetidin-1-yl)ethyl]-2-imidazolidinone This product is obtained substantially as in the foregoing example, starting from 3-chloro-4,6-dimethoxyaniline and by operating substantially as in Examples 4, 3, and 1, but using an excess of ethanthiole.

EXAMPLE 11

The followings are three different types of capsules which contains different amounts of the compound of Example 1:

|  | A | B | B |
| --- | --- | --- | --- |
| Compound of example 1 | 5 mg | 20 mg | 50 mg |
| Mg stearate | 5 mg | 5 mg | 5 mg |
| Carboxymethylcellulose | 10 mg | 10 mg | 10 mg |
| Starch | 180 mg | 165 mg | 135 mg |

What is claimed is:

1. The compound 1-(3-chloro-4-hydroxyphenyl)-3-[2-(3,3-dimethylazetidin-1-yl)ethyl]-2-imidazolidinone or a pharmaceutically acceptable salt thereof.

2. The compound 1-(4-acetoxy-3-chlorophenyl)-3-[2-(3,3-dimethylazetidin-1-yl)ethyl]-2-imidazolidinone or a pharmaceutically acceptable salt thereof.

3. A method of relieving the symptoms of neuroses and psychoses in a person in need thereof which comprises the daily administration of from 0.2 mg to 3.0 mg/kg of a compound of claim 1 or a pharmaceutically acceptable salt thereof.

4. A method of relieving the symptoms of neuroses and psychoses in a person in need thereof which comprises the daily administration of from 0.2 mg to 3.0 mg/kg of a compound of claim 2 or a pharmaceutically acceptable salt thereof.

* * * * *